(12) United States Patent
Mather

(10) Patent No.: US 7,151,157 B2
(45) Date of Patent: Dec. 19, 2006

(54) MECHANICALLY ACTIVATED SHAPE MEMORY DEVICE

(75) Inventor: Patrick T. Mather, Chagrin Falls, OH (US)

(73) Assignee: University of Connecticut, Storrs, CT (US)

( * ) Notice: Subject to any disclaimer, the term of this patent is extended or adjusted under 35 U.S.C. 154(b) by 0 days.

(21) Appl. No.: 11/072,066

(22) Filed: Mar. 4, 2005

(65) Prior Publication Data

US 2005/0197488 A1    Sep. 8, 2005

Related U.S. Application Data

(60) Provisional application No. 60/549,949, filed on Mar. 4, 2004.

(51) Int. Cl.
*C08F 6/00* (2006.01)
(52) U.S. Cl. .......................... 528/480; 347/20; 347/54; 347/94
(58) Field of Classification Search ............... 347/20, 347/54, 94; 528/480; 606/41
See application file for complete search history.

(56) References Cited

U.S. PATENT DOCUMENTS

| | | |
|---|---|---|
| 4,077,390 A | 3/1978 | Stanley et al. |
| 4,296,801 A | 10/1981 | Guex et al. |
| 4,379,448 A | 4/1983 | Kapralis et al. |
| 4,460,546 A | 7/1984 | Kapralis et al. |
| 4,532,110 A | 7/1985 | Kapralis et al. |
| 4,572,158 A | 2/1986 | Fiedler |
| 4,580,547 A | 4/1986 | Kapralis et al. |
| 4,829,980 A | 5/1989 | Smith |
| 4,831,094 A | 5/1989 | Stein et al. |
| 4,899,727 A | 2/1990 | Kapralis et al. |
| 5,056,589 A | 10/1991 | Hettel et al. |
| 5,058,563 A | 10/1991 | Manker |
| 5,143,048 A | 9/1992 | Cheney, III |
| 5,145,935 A | 9/1992 | Hayashi |
| 5,275,156 A | 1/1994 | Milligan et al. |
| 5,305,733 A | 4/1994 | Walters |
| 5,339,796 A | 8/1994 | Manker |
| 5,506,300 A | 4/1996 | Ward et al. |
| RE35,586 E | 8/1997 | Manker |
| 5,665,822 A | 9/1997 | Bitler et al. |
| 5,915,461 A | 6/1999 | Tanhehco |
| 6,007,504 A | 12/1999 | Bailey et al. |
| 6,537,309 B1 | 3/2003 | Sharma et al. |
| 6,866,805 B1* | 3/2005 | Hong et al. .................. 264/161 |
| 6,918,138 B1* | 7/2005 | Donovan ........................ 2/174 |
| 2001/0031963 A1* | 10/2001 | Sharkey et al. ............... 606/41 |
| 2004/0123490 A1* | 7/2004 | Pancheri et al. .............. 34/597 |
| 2005/0050611 A1* | 3/2005 | Donovan ........................ 2/174 |

OTHER PUBLICATIONS

"Smart Fibres, Fabrics and Clothing"edited by Xiaoming Tao; Oct. 2000, 1-5 pages.*
Fibrous materials in healthcare and biomedical applications Proceeding of the Health & Textile Conference, Jan. 18-19, 2001, Biella, Italy Shishoo, R.*
Irie, M. "Shape Memory Polymers", Cambridge University Press: Cambridge, UK, 1998, pp. 203-219.
H. G. Leon et al., "Shape Memory and Nanostructure in Poly(Norbornyl-POSS) Copolymers, Polymer International, vol. 49, No. 5, pp. 453-457 (2000).
C. Liu et al., "Chemically Cross-Linked Polycyclooctene: Synthesis, Characterization, and Shape Memory Behavior", Macromolecules, vol. 35, No. 27, pp. 9868-9874 (2002).

* cited by examiner

*Primary Examiner*—Terressa Boykin
(74) *Attorney, Agent, or Firm*—Cantor Colburn LLP

(57) ABSTRACT

A device and method are provided combining the thermal and mechanical attributes of two distinct materials: shape memory materials and super-cooled liquids (SCLs). In one example of the invention, the super-cooled liquid is contained within a shape memory polymer (SCL liquid is filled into a shape memory polymer tube), so that the heat released by the SCL when it is mechanically triggered to crystallize itself triggers the shape change of the shape memory polymer. The device is suitable as a reusable warmer, as a dental mold material, in medical applications where reusable heat packs are indicated, particularly for application to difficult contours, and for large deployable structures such as satellite antennae and temporary shelters.

18 Claims, 1 Drawing Sheet

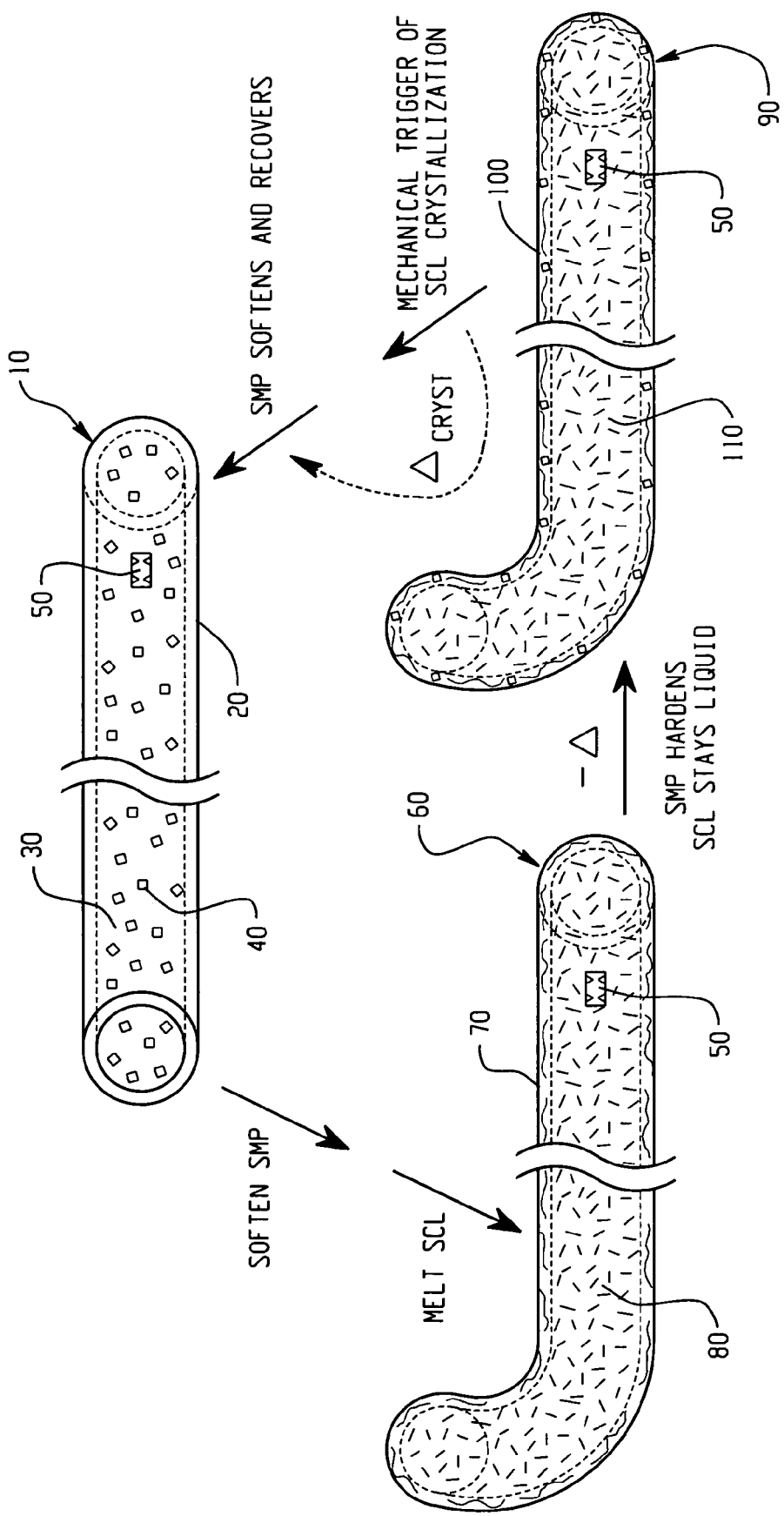

MECHANICALLY ACTIVATED SHAPE MEMORY DEVICE

CROSS REFERENCE TO RELATED APPLICATIONS

This application claims the benefit of U.S. Provisional Patent Application Ser. No. 60/549,949, filed Mar. 4, 2004.

FIELD OF THE INVENTION

This invention relates to a method of mechanically activating the shape recovery of a deformed shape memory material. The invention also relates to a device comprising a mechanically activated shape memory material.

BACKGROUND OF THE INVENTION

Shape memory is the ability of a material to remember its original shape, either after mechanical deformation, which is a one-way effect, or by cooling and heating, which is a two-way effect. This phenomenon is based on a structural phase transformation.

Materials known to have these properties are shape memory alloys (SMAs), for example TiNi, CuZnA1, and FeNiA1 alloys. The structure phase transformation of these materials is known as a martensitic transformation. These materials have been proposed for various applications such as vascular stents, medical guidewires, orthodontic wires, vibration dampers, pipe couplings. However, these materials have not been widely used, in part due to their relatively high costs and their limited range of mechanical properties.

Shape memory polymers (SMPs) have been under active development as a replacement or augmentation to SMAs. SMPs enjoy many advantages, among which are low density, high recoverable strain (up to several hundred percent compared to less than 8% for SMA), tailorability of the transition temperature and rubbery modulus according to the application, easy processability, and economy of materials and manufacturing. In the literature, several classes of polymers have been shown to allow SMP behavior, including highly entangled amorphous polymers, crosslinked amorphous polymers (including castable SMPs), melt-miscible blends of semicrystalline and amorphous polymers, crosslinked semicrystalline polymers and their blends with rubber (shape memory rubber), and multiblock copolymers. The latter SMP class consists of phase-segregated linear block co-polymers having a hard segment and a soft segment. The hard segment is typically crystalline, with a defined melting point, and the soft segment is typically amorphous, with a defined glass transition temperature. In some embodiments, the hard segment is amorphous and has a glass transition temperature rather than a melting point. In other embodiments, the soft segment is crystalline and has a melting point or glass transition temperature. The melting point or glass transition temperature of the soft segment is substantially lower than the melting point or the glass transition temperature of the hard segment.

When the SMP is heated above the melting point or glass transition temperature of the hard segment, the material can be shaped with complete relaxation of internal stress. This original shape can be memorized by cooling the SMP below the melting point or glass transition temperature of the hard segment. When the shaped SMP is cooled below the melting point or glass transition temperature of the soft segment while the shape is deformed, that temporary shape is fixed. The original shape is recovered by heating the material above the melting point or glass transition temperature of the soft segment but below the melting point or glass transition temperature of the hard segment. In another method for setting a temporary shape, the material is deformed at a temperature lower than the melting point or glass transition temperature of the soft segment. When the material is heated above the melting point or glass transition temperature of the soft segment, but below the melting point or glass transition temperature of the hard segment, the stresses and strains are relieved and the materials return to their original shape. The recovery of the original shape, which is induced by an increase in temperature, is called the thermal shape memory effect.

The shape memory effects are intimately linked to the polymer's structure and morphology and exist in many polymers, copolymers and cross-linked polymers. Examples of polymers used to prepare hard and soft segments of SMPs include various polyethers, polyacrylates, polyamides, polysiloxanes, polyurethanes, polyethers amides, polyurethane/ureas, polyether esters (U.S. Pat. No. 5,506,300 to Ward et al., U.S. Pat. No. 5,145,935 to Hayashi, and U.S. Pat. No. 5,665,822 to Bitler et al), polynorborene (Japanese Patent Publication No. JP 59-53528 (Nippon Zeon Co. Ltd)) cross-linked polymers such as cross-linked polyethylene and cross-linked poly(cyclooctene) (C. Liu, S. B. Chun, P. T. Mather, L. Zheng, E. H. Haley, and E. B. Coughlin, *Macromolecules*, volume 35, number. 27, pages 9868–9874 (2002)), inorganic-organic hybrid polymers (H. G. Leon, P. T. Mather, and T. S. Haddad, *Polymer International*, volume 49, number 5, pages 453–457 (2000)), and copolymers such as urethane/butadiene copolymers, styrene-butadiene copolymers (M. Irie, Chapter 9: Shape Memory Polymers, in K. Otsuka and C. M. Wayman, eds., "Shape Memory Materials," Cambridge University Press: Cambridge, UK, 1998).

As described above, the recovery of the original shape of a SMP or SMA is triggered by the application of heat that increases the temperature of the SMP or SMA beyond the critical temperature, be it a melting point or glass transition temperature. To date, application of heat has been primarily from external sources, such as heat guns, or hot water. However, new applications of shape memory materials would be possible if the heat necessary to allow shape recovery in a shape memory material were generated within or immediately adjacent to the shape memory article itself.

BRIEF DESCRIPTION OF THE INVENTION

The invention comprises a device combining the advantages of a shape memory material and a super-cooled liquid containing heat pack provided with a crystallization trigger or activator. The super-cooled liquid and its crystallization activator/trigger provide mechanical activation of shape or strain recovery in shape memory materials that avoids the use of external heating at the time of the shape recovery, thereby greatly extending the range of applications available for the device.

SMP or SMA is used in fabricating the container or as an integral element of the container for the super-cooled liquid. Preferably the device, i.e., the container portion thereof is made of an SMP. Mechanical activation of the super-cooled liquid to allow initiation of heat-generating crystallization results in the triggering of strain recovery of the SMP toward a deployed shape that is rigid and stationary until later heated for simultaneous liquification of the super-cooled liquid and softening of the SMP for strain fixing in a temporary (generally compact) shape.

The device is suitable as a reusable warmer, as a dental mold material, in medical applications where reusable heat packs are indicated, particularly for application to difficult contours, and for large deployable structures such as satellite antennae and temporary shelters

BRIEF DESCRIPTION OF THE DRAWING

The FIGURE shows an embodiment in which a shape memory article comprising a super-cooled liquid within a shape memory polymer is heated to soften the shape memory polymer and melt the previously crystallized super-cooled liquid, reshaped to a nonequilibrium shape, cooled to harden the shape-memory polymer into the nonequilibrium shape, and mechanically activated to trigger crystallization of the super-cooled liquid thereby softening the shape memory polymer and allowing recovery of the equilibrium shape and concomitant hardening of the super-cooled liquid.

DETAILED DESCRIPTION OF THE INVENTION

The present invention provides a means for shape or strain recovery in shape memory materials using heat generated from the crystallization of a super-cooled liquid. The use of super-cooled liquid eliminates the need to use an external heating source, such as a heat gun, electrical heating element, and the like. Without the necessity of an external heating element, the portability of the device and the ease of using it are greatly enhanced.

A particular source of heat, heat pack, has been used for many years by sportsmen and others to warm parts of the human body for therapeutic purposes or simply fending off the cold. One particularly favored embodiment of the heat pack is the reusable heat pack employing a super-cooled liquid and an activator. A super-cooled liquid is a liquid that can cool well below the normal liquid-to-solid phase change temperature, but still remain in the liquid phase. Normally the super-cooled liquid is prepared so that it remains stable at ambient temperature found in homes, hospitals and their related storage areas. When the pack is to be used, crystallization in the solution is initiated. Thus, when an activator embedded in the super-cooled liquid is triggered, conditions are created in the liquid that cause the material to change very rapidly, in wave like manner from the activation site, from the liquid phase to the solid phase, thus quickly giving up the heat of crystallization to the surroundings. The super-cooled liquid can be made from many different materials, including aqueous solutions of sodium acetate, calcium nitrate, lead acetate, sodium borate, sodium phosphate, sodium pyrophosphate, sodium thiosulfate, trimethylol ethane (U.S. Pat. No. Re. 35,586 to Manker, and U.S. Pat. No. 6,537,309 to Sharma et al.) and their hydrates, and the melt or supersaturated solution xylitol (U.S. Pat. No. 4,296,801 to Guex). The aqueous solution of sodium acetate is typically preferred because it is generally harmless to humans.

The salt solution is made by dissolving the salt in the desired amount of water. The amount of salt to be utilized should permit the salt solution to be super-cooled to at least the ambient temperature at which the heat pack is intended to be utilized. Additionally, the amount of the salt should not be so great that the resulting solution is activated unintentionally by shaking, etc., when at ambient or use temperature. However, a sufficient amount of salt should be used to enable the super-cooled solution to be readily crystallized when the trigger is activated and to release sufficient heat to serve the desired function. In particular, the amount of water present in the salt solution will vary depending upon the heat pack temperature desired. As the amount of water increases relative to the amount of salt, the temperature to which the container contents are raised when the salt crystallizes decreases. This means that the maximum temperature of a heat pack can be controlled by appropriate adjustment of the water/salt ratio (U.S. Pat. No. 5,305,733 to Walters).

Optionally, various gelling agents can be added to prevent the super-cooled aqueous solution from freely flowing (also known as "saddlebagging") giving rise to uneven heating (U.S. Pat. No. Re. 35,586 to Manker, and U.S. Pat. No. 5,058,563 to Manker). Various other compounds can also be added to the super-cooled solution to impart desirable properties, such as the addition of aniline to increase the shelf life of the product (U.S. Pat. No. 6,537,309 to Sharma et al), the addition of viscosity enhancing compounds for improved smoothness to the crystallized solution (U.S. Pat. No. 6,537,309 to Sharma et al.), and the like.

The triggering of the super-cooled solution to activate the crystallization has been accomplished in a number of ways. Puncturing devices can be used in the presence (U.S. Pat. No. 5,915,461 to Panhehco) or absence (U.S. Pat. No. 5,305,733 to Walters) of salt crystals. U.S. Pat. No. 5,275,156 to Milligan et al. and U.S. Pat. Nos. 4,460,546, 4,580,547, and 4,899,727 all to Kapralis et al. disclose various trigger devices that float free in the super-cooled salt solution, which is activated by mechanically stressing the devices. U.S. Pat. No. 5,056,589 to Hettel et al. discloses the use of a metallic spring mechanism for crystallizing a super-cooled salt solution, and U.S. Pat. No. 5,143,048 to Cheney discloses a disc or ampoule containing crystals of the salt used to form the super-cooled salt solution. U.S. Pat. No. 4,077,390 to Stanley et al., U.S. Pat. Nos. 4,379,448 and 4,460,546 and 4,532,110 to Kapralis et al., and U.S. Pat. No. 4,572,158 to Fiedler disclose the use of strips with slits or openings in contact with the super-cooled solution wherein the bending or flexing of the strips initiates the crystallization. U.S. Pat. No. 4,829,980 to Smith discloses the use of nested helically-coiled resilient metallic filament as a trigger.

The shape memory material used in this invention can be of any suitable shape memory polymer or alloy formulations as described above, such as castable shape memory formulations, shape memory rubber, amorphous/crystalline blends, and/or nanostructured biodegradable SMP polyurethanes. The preferred materials are shape memory polymers, particularly a cured blend of poly(cyclooctene) and styrene-butadiene rubber.

The super-cooled liquid can be selected from the ones described above. The preferred super-cooled liquid is an aqueous sodium acetate solution (preferably about 40 to about 60 weight percent, more preferably roughly 50 weight percent) prepared by dissolving sodium acetate or its hydrates in an appropriate amount of water. The purity of the sodium acetate and water should be such that no impurity, such as dust, is present to trigger an unintentional premature crystallization.

It is within the spirit of the invention to add various agents into the super-cooled salt solution to impart desirable properties, such as the addition of gelling agents (U.S. Pat. Nos. Re. 35,586 and 5,058,563 to Manker) to prevent uneven heating, and/or the addition of shelf life enhancement agents (U.S. Pat. No. 6,537,309 to Sharma et al.), and viscosity adjusting compounds (U.S. Pat. No. 6,537,309 to Sharma et al.).

The trigger/activator can be selected from the ones described above. The preferred embodiment uses a fissure-containing stainless steel strip, such as that disclosed in U.S. Pat. No. 4,077,390 to Stanley et al.

An illustrative procedure for making the mechanically activated shape memory device of the invention is shown in the Figure. A shape memory device 10 in its equilibrium conformation comprises walls having a hardened, unstrained shape memory polymer 20 (such as a slender tube from a cured blend of poly(cyclooctene) and styrene-butadiene rubber), a saturated salt solution 30 (e.g., a saturated, aqueous solution of sodium acetate), solid salt crystals 40 (e.g., sodium acetate crystals), and a trigger strip 50 in contact with the saturated salt solution. The opening in the tube through which the salt solution is introduced is subsequently vacuum sealed. The shape memory device 10 is heated to a temperature above the melting point or glass transition temperature of the shape memory polymer and also above a temperature sufficient to dissolve the salt crystals 40. This heating softens the hardened shape memory polymer 20 to yield a shape memory device comprising softened shape memory polymer 70 and a solution 80 into which the solid solute particles 40 have dissolved. For example, heating to about 65° C. or higher is sufficient to soften the poly (cyclooctene) fixing phase of the blend of poly(cyclooctene) and styrene-butadiene rubber and to melt the crystallized aqueous sodium acetate solution. The shape memory device is then reshaped (e.g., by twisting, stretching, folding, rolling, etc.; reshaping process not shown) to yield a shape memory device 60 in its temporary, nonequilibrium conformation. Cooling the shape memory device 60 (e.g., with air or water) yields shape memory device 90 in which the shape memory polymer 100 has hardened in a strained conformation and the salt solution 110 is super-cooled. When maintained at room temperature, the super-cooled liquid in the device is metastable against crystallization and remains as a liquid, while the shape memory polymer is in a temporary (deformed) shape and is stable against strain recovery. Activation of the trigger strip 50 (e.g., as described in U.S. Pat. No. 4,077,390 to Stanley et al.) initiates crystallization in the super-cooled solution, generating heat that temporarily softens the hardened and strained shape memory 90 to yield a softened shape memory polymer (not shown) and allows the shape memory device to reassume its equilibrium conformation. For example, when the super-cooled solution is a supersaturated sodium acetate solution, crystallization will release about 190 Joules per gram of energy at a crystallization temperature that varies with the water content, but is in the range $35 < T_{cryst} < 58°$ C. The sodium acetate concentration in the supercooled solution may therefore be selected so that the crystallization temperature is greater than the critical temperature for the onset of shape recovery $T_{cryst}$ (about 40 to 50° C. for this example). Energetically, the work performed by the shape memory polymer upon shape/strain recovery may be derived from the mechanical work done in performing the original shape fixing, but some additional energy may be derived from the heat released from the crystallization of the super-cooled liquid. The crystallization may progress as a front and thus the shape recovery may occur as a smooth propagation ideal for deployment of a complex structure. Alternatively, deployment of the structure could commence from at least two sites simultaneously or sequentially as dictated by the locations of at least two mechanical triggering sites.

The amount of water utilized with super-cooled liquid, as described above, can influence the temperature the device can heat up to upon crystallization, with a lower water concentration leading to a higher temperature. Therefore, depending on the kind of shape memory material employed in making the device, the amount of water (or the kind of super-cooled liquid) can be varied to provide a temperature suitable for the triggering the shape recovery of the SMP. A particular advantage of using low water content is that the final deployed device (after crystallization and shape recovery) is more robust due to the presence of rigid solid crystals.

The devices of the invention are suitable as reusable warmers, as molding materials for making impressions as for example of dental tissue and in numerous medical applications where reusable heat packs are indicated particularly for application to difficult contours. Additionally, large expandable structures, including satellite antennae and temporary shelter, are envisioned with the possibility of remote radio-frequency (RF) activation of the mechanical trigger that, in this case, would feature a small motor and RF antenna.

All cited patents, patent applications, and other references are incorporated herein by reference in their entirety.

The invention claimed is:

1. A method for inducing the shape/strain recovery of a shape memory article, wherein the shape memory article comprises a super-cooled liquid in a container comprising a shape memory polymer, and wherein inducing the shape/strain recovery of the shape memory article comprises using heat generated from crystallization of the super-cooled liquid upon mechanical activation thereof.

2. The method according to claim 1, wherein said shape memory material is a shape memory polymer; and wherein said shape memory polymer is a cured blend of poly (cyclooctene) and styrene-butadiene rubber.

3. The method according to claim 1, wherein said super-cooled liquid is an aqueous solution of sodium acetate.

4. The method according to claim 3, wherein said sodium acetate is present in an amount of about 40 to about 60 weight percent, based on the weight of the super-cooled liquid.

5. The method according to claim 1, wherein said mechanical activation is achieved using a fissure-containing stainless steel strip.

6. The method according to claim 5, wherein said mechanical activation is achieved by bending or flexing the strip.

7. The method according to claim 1, wherein said mechanical activation comprises remote triggering using a miniature motor and radio-frequency antenna.

8. The method according to claim 1, wherein said mechanical activation comprises activating at least two mechanical triggering sites.

9. A device comprising a container formed from a shape memory material, a super-cooled liquid provided in said container and a mechanical trigger provided in said container in contact with said super-cooled liquid for initiating crystallization thereof; wherein said shape memory material is a shape memory polymer; and wherein said device is adapted to induce shape/strain recovery of the shape memory material using heat generated from crystallization of the super-cooled liquid upon mechanical activation thereof by the mechanical trigger.

10. The device according to claim 9, wherein said shape memory polymer is a cured blend of poly(cyclooctene) and styrene-butadiene rubber.

11. The device according to claim 9 wherein said super-cooled liquid is an aqueous solution of sodium acetate.

12. The device according to claim 11, wherein said sodium acetate trihydrate is present in an amount of about 40 to about 60 weight percent, based on the weight of the super-cooled liquid.

13. The device according to claim 9, wherein said mechanical activation device is a fissure-containing stainless steel strip.

14. The device according to claim 13, wherein said mechanical activation device is activated by bending or flexing the strip.

15. The device according to claim 9, wherein said mechanical trigger comprises a miniature motor and radio-frequency antenna allowing remote triggering.

16. The device according to claim 9, wherein said mechanical trigger comprises at least two mechanical triggering sites.

17. The method according to claim 1, wherein said shape memory polymer is selected from highly entangled amorphous polymers, crosslinked amorphous polymers, melt-miscible blends of semicrystalline and amorphous polymers, crosslinked semicrystalline polymers, blends of crosslinked semicrystalline polymers and rubber, and multiblock copolymers having a hard segment and a soft segment.

18. The device according to claim 9, wherein said shape memory polymer is selected from highly entangled amorphous polymers, crosslinked amorphous polymers, melt-miscible blends of semicrystalline and amorphous polymers, crosslinked semicrystalline polymers, blends of crosslinked semicrystalline polymers and rubber, and multiblock copolymers having a hard segment and a soft segment.

* * * * *